United States Patent [19]
Schoenberg et al.

[11] Patent Number: 5,616,722
[45] Date of Patent: Apr. 1, 1997

[54] ANTIMICROBIAL SOLUTION OF FORMALDEHYDE SUBSTITUTED HYDANTOIN AND PROCESS FOR PREPARATION

[75] Inventors: Thomas G. Schoenberg, Lemont; Richard J. Otterson, Olympia Fields; Darrell J. Zehner, Plainfield, all of Ill.

[73] Assignee: McIntyre Group, Ltd., University Park, Ill.

[21] Appl. No.: 567,150

[22] Filed: Dec. 5, 1995

[51] Int. Cl.$^6$ .................... C07D 233/78; C07D 233/72; C07D 233/74; A61K 31/415
[52] U.S. Cl. .................... 548/319.1; 548/317.1
[58] Field of Search .................... 548/319.1; 514/389

[56] References Cited

U.S. PATENT DOCUMENTS

| | | | |
|---|---|---|---|
| 3,987,184 | 10/1976 | Foelsch | 514/389 |
| 4,172,140 | 10/1979 | Shull et al. | 424/273 R |
| 4,496,571 | 1/1985 | Loncrini et al. | 514/389 |
| 5,037,843 | 8/1991 | Schoenberg et al. | 514/389 |
| 5,252,744 | 10/1993 | Farina et al. | 548/317.1 |

FOREIGN PATENT DOCUMENTS

| | | | |
|---|---|---|---|
| 4-360873 | 12/1992 | Japan | 548/319.1 |

OTHER PUBLICATIONS

Aisenberg, Irwin M., *Attorney's Dictionary of Patent Claims*, Matthew Bender, 1, C–27–C–29, (1996).
"Cosmetic Preservatives Encyclopedia—Antimicrobials", *Cosmetics & Toiletries*, 105, 49, 49, 56, (1990).
Derwent English Language Abstract of Mitsui Japanese Published Patent Application No. 4,360,873. (1992).
"*Cosmetic Preservatives,*" *excerpt from Complete Guide to the McIntyre Group Product Line*, 18, McIntyre Group. Ltd. (1993).
Muscatiello, M.J. "CTFA's Preservation Guidelines," *Cosmetics & Toiletries*, 108, 53, 56–59 (1993).
Mulberry, G.K., et al., "Rapid Screening Methods for Preservative Efficacy Evaluations," *Cosmetics & Toiletries*, 102, 47–50, 51–54 (1987).
Parsons, T., "A Microbiology Primer for the Microbiology Manager," *Cosmetics & Toiletries*, 105, 73–77 (1990).
"Preservative Mixture Encyclopedia Update," *Cosmetics & Toiletries*, 108, 89–91 (1993).
Parker, Malcolm S. "Preservatives in Combination," *Soap, Perf., Cosmet.*, 223–224 (Apr. 1973).

*Primary Examiner*—Floyd D. Higel
*Attorney, Agent, or Firm*—Olson & Hierl, Ltd.

[57] ABSTRACT

A method of preparing a formaldehyde substituted hydantoin in the form of a liquid antimicrobial preservative solution is disclosed. The inventive solution prepared by the disclosed method comprises a condensation product of a 5,5-disubstituted hydantoin and formaldehyde prepared in the presence of an antimicrobial liquid phenylic or benzylic alcohol. The inventive solution inhibits or retards microbial growth when an effective microbial inhibiting amount is subsequently added to a medium capable of supporting undesirable microbial growth. Preferably the inventive solution contains 1,3-dimethylol-5,5-dimethyl hydantoin prepared in the presence of phenoxyethanol and including an effective antimicrobial amount of at least one paraben preservative prepared by an embodiment of the disclosed method.

13 Claims, No Drawings

# ANTIMICROBIAL SOLUTION OF FORMALDEHYDE SUBSTITUTED HYDANTOIN AND PROCESS FOR PREPARATION

FIELD OF THE INVENTION

This invention lies in the field of antimicrobial solutions of formaldehyde substituted hydantoin.

BACKGROUND OF THE INVENTION

Solutions of a formaldehyde substituted hydantoin, such as 1,3-dimethylol-5,5-dimethyl hydantoin (DMDM hydantoin), prepared in an anhydrous liquid solvent such as a polyhydroxy alcohol and/or an alkylene carbonate have previously been disclosed (see Schoenberg U.S. Pat. No. 5,037,843 issued Aug. 6, 1991). Such solutions particularly those employing propylene glycol as the solvent, now enjoy commercial success and display antimicrobial activity when used as preservative systems in personal care, cosmetic, and household products at use concentrations of typically less than about 1 weight percent of the product. Although in the Schoenberg solutions the solvents themselves are readily water miscible, they display no antimicrobial activity at the use concentrations employed.

For certain formulations, however, formulators now desire to incorporate as a preservative an aromatic alcohol particularly because such an alcohol can both demonstrate antimicrobial activity and be in liquid form. Such aromatic alcohols have a limited solubility in water.

It has now been discovered that formaldehyde substituted hydantoin is compatible with and soluble in such an antimicrobial liquid aromatic alcohol. Thus it would appear that a desirable antimicrobial solution for use as a preservative in the cosmetic field could be prepared by simply physically dissolving a formaldehyde substituted hydantoin in such an aromatic alcohol. However, such physical blends are not available as articles of commerce and hence must be prepared by the user from separate components in multistep procedures. Thus, there is a need and desire in the trade for liquid solutions of a formaldehyde substituted hydantoin in such an aromatic alcohol.

It is not practical to reprocess a Schoenberg solution to remove therefrom the Schoenberg solvent medium and to replace same with such a liquid aromatic alcohol. Also, addition of such an aromatic alcohol to a previously prepared Schoenberg solution is not practical because such addition reduces the concentration of resulting antimicrobial agents in the solution as diluted.

In order to supply to the using trade a solution of a formaldehyde substituted hydantoin in an aromatic alcohol, it is necessary to prepare an antimicrobial preservative solution which is not only an effective liquid preservative that is compatible with formulations with which it is to be used, but is also shelf stable at ambient conditions and economical to use. However, merely substituting a liquid aromatic alcohol for a polyhydroxy alcohol and/or alkylene carbonate in a solution preparation process such as described by Schoenberg in the '843 patent does not result in a practical preparation process because the solubility characteristics of the aromatic alcohols present different compatibility, stability and liquidity problems. A new and commercially practical process for directly preparing and synthesizing antimicrobial solutions of formaldehyde substituted hydantoin in an aromatic alcohol would be desirable.

The present invention provides both such a new and commercially practical direct synthetic process and new resulting product solutions which have unexpected value as antimicrobial liquid preservatives.

SUMMARY OF THE INVENTION

In one aspect, this invention relates to a new and very useful process for directly preparing an antimicrobial liquid solution comprising an in situ synthesized formaldehyde substituted hydantoin in an antimicrobial liquid aromatic alcohol.

In another aspect, this invention relates to new and very useful antimicrobial solutions which are produced by the present inventive process and wherein the solutes and the solvent surprisingly and unexpectedly coact in a synergistical manner to provide improved antimicrobial effectiveness when the inventive solutions are included in a dilute but effective antimicrobial amount in a medium capable of supporting microorganism growth.

The inventive antimicrobial solutions are suitable for use in, for example, personal care, cosmetic and household products. These inventive solutions apparently also display low toxicity and low skin irritation yet are compatible at use concentrations with the commonly used ingredients in such products.

The inventive solutions can also be prepared so as to have extended shelf life and be cold stable.

The inventive antimicrobial solution preparation process is relatively simple, reliable and cost effective. It is well suited for commercial scale practice.

The inventive process achieves the desired goal of providing solutions of formaldehyde substituted hydantoin in combination with liquid antimicrobial aromatic alcohol at a commercially acceptable cost. In these solutions, each of the formaldehyde substituted hydantoin and the liquid aromatic alcohol can be present at concentration levels which display antimicrobial activity.

Important for purposes of process operability is the discovery that members of a narrow class of aromatic liquids, generally antimicrobially active phenylic and benzylic alcohols, are suitable as hereinbelow characterized. Also, controlled process conditions and steps are needed.

Unexpectedly, the inventive solutions produced by the practice of the inventive process generally display greater antimicrobial activity than either the formaldehyde substituted hydantoin used alone (for example, in a solvent which is antimicrobially substantially inert) or the liquid aromatic alcohol used alone. Characteristically, the antimicrobial activity achievable with the inventive solutions appears to be greater than the comparable activity observed with, for example, the Schoenberg solutions of the '843 patent (above identified).

Other and further objects, aims, features, advantages, purposes, embodiments, applications and the like will be apparent to those skilled in the art from the present specification taken with the appended claims.

DETAILED DESCRIPTION OF THE INVENTION

The formaldehyde substituted hydantoins, as known to the prior art (see, the discussion in Schoenberg U.S. Pat. No. 5,037,843 which is incorporated herein by reference), are produced by reacting formaldehyde with a 5,5-disubstituted hydantoin wherein each substituent group on the hydantoin ring is independently selected from the class consisting of phenyl and lower alkyl groups containing 1 to about 6 carbon atoms per group.

Exemplary 5,5-disubstituted hydantoins include 5,5-dimethyl hydantoin (DMH), 5-methyl-5-ethylhydantoin, 5,5-diethylhydantoin, 5,5-diphenylhydantoin, 5-methyl-5 -phenylhydantoin, 5,5-pentamethylenehydantoin and the like known in the art as possessing broad spectrum bactericidal or fungicidal activity. DMH is particularly preferred.

The reaction with formaldehyde introduces methylol groups bound to the nitrogen atom at each of the 1 and/or 3 positions of the hydantoin ring.

The liquid aromatic alcohols usable in the practice of the present invention are characterized by the formula:

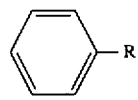

(1)

wherein R is selected from the group consisting of —CH$_2$OH, —OCH$_2$—OH, —OCH$_2$CH$_2$OH, —CH$_2$CH$_2$OH, —OC$_3$H$_6$OH, and —C$_3$H$_6$OH.

Preferred formula (1) compounds are phenoxyethanol (presently most preferred), benzyl alcohol, phenethyl alcohol, and phenoxyisopropyl alcohol all of which are known to have antimicrobial activity.

To practice the process of this invention, one initially dissolves, preferably under substantially anhydrous conditions, paraformaldehyde in at least one aromatic alcohol of formula (1). Alternatively, the formaldehyde can be added as formalin, preferably methanol free and at a concentration of at least about 30 weight percent formaldehyde. Paraformaldehyde is preferred.

The resulting liquid medium preferably contains at least about 2 weight percent, and, more preferably in the range of 10 to about 25 weight percent of total calculated formaldehyde on a 100 weight percent total liquid medium basis. With respect to paraformaldehyde, the term "substantially anhydrous" denotes paraformaldehyde which is at an active concentration of above about 90 weight percent, preferably at about 95 weight percent or more based on total starting paraformaldehyde composition.

The resulting liquid medium is then heated to a temperature in the range of about 30° to about 55° C., and, more preferably, about 35° to about 50° C. Thereafter a 5,5-disubstituted hydantoin (such as above characterized) is admixed into (and dissolved in) the so-heated liquid medium, thereby to produce a reaction mixture. In this reaction mixture, the amount of the 5,5-disubstituted hydantoin present is at least sufficient to produce in the reaction mixture an initial calculated mole ratio of formaldehyde to the substituted hydantoin of about 1:1 to about 3:1 and, more preferably, in the range of about 1.5:1 to about 2.1:1.

Next, the resulting reaction mixture is heated under autogenous pressure conditions (to avoid loss of volatile components) to a temperature in the range of about 60° to about 120° C., more preferably in the range of about 80° to about 110° C., over a reaction period of about 2 to about 14 hours. A liquid phase condensation reaction ensues between the paraformaldehyde and the 5,5-disubstituted hydantoin. Characteristically, the condensation product contains a mixture of methylol substituted 5,5-disubstituted hydantoin with the methylol substituents being in the 1 and/or 3 positions. However, the reaction conditions influence the condensation product produced so that very high yields of 1,3-dimethylol substituted 5,5-disubstituted hydantoins can be produced, as preferred.

A temperature in this range for the resulting reaction mixture is maintained until this reaction is substantially complete as determined by the point where the amount of free formaldehyde present in the reaction mixture is below about 2 weight percent based on total reaction mixture weight. To reach such a free formaldehyde content, it may be desirable to add additional 5,5-disubstituted hydantoin to the reaction mixture.

Thereafter, the resulting reaction mixture is cooled to ambient temperature. Optionally this mixture is filtered to remove any particulates and to clarify the mixture. Preferably, the filter has submicron pore size. This mixture is an antimicrobial solution of the invention comprising a formaldehyde substituted hydantoin formed in situ and dissolved in a liquid aromatic alcohol of formula (1).

Preferably, in such a product antimicrobial solution, the total amount of formaldehyde substituted (i.e., methylol substituted) hydantoin ranges from about 15 to about 70 weight percent while the amount of formula (1) aromatic alcohol preferably ranges from about 30 to about 80 with the balance up to 100 weight percent of the solution being unreacted components (formaldehyde and 5,5-disubstituted hydantoin) and reaction byproducts (such as water) or additives such as hereinbelow indicated. Preferably, a product solution contains at least about 10 weight percent of dimethylol substituted 5,5-disubstituted hydantoin on a 100 weight percent total hydantoin condensate product basis.

If desired, as those skilled in the art will appreciate, the water of reaction can be removed by stripping or the like, thereby to produce an anhydrous product.

Although such a product solution displays excellent antimicrobial activity, so that it can be used as a preservative, it has been found that the spectrum of antimicrobial activity of a product solution can be still further broadened by the use of certain additives. For example, it is known that monomethylol and dimethylol condensation products of 5,5-dimethyl hydantoin have broad spectrum antibacterial activity at use concentrations of about 0.01 to about 1 weight percent but are less effective against yeasts. Phenoxyethanol, per se is a weaker antimicrobial agent, but is reportedly effective against a broad range of gram-negative bacteria at use concentrations of about 0.5 to about 2 weight percent.

It has been found that addition and dissolution of a relatively small amount of one or more paraben esters improves the solution antimicrobial activity still further. The paraben ester can be added at any point in the synthesis procedure preferably to the resulting reaction mixtures while heat is still being applied thereto so that paraben ester dissolution is enhanced. The paraben esters enhance the product solution bacteriostatic activity against gram positive bacteria fungi. The term "paraben ester" has conventional reference herein to phenyl esters of parahydroxybenzoic acid and alkyl esters of parahydroxybenzoic acid wherein the alkyl group includes 1 to about 10 carbon atoms.

The addition to the reaction mixture of paraben ester is more preferably accomplished after substantial reaction takes place between the formaldehyde and the substituted hydantoin. Alternatively, and more preferably, the paraben ester is added to the reaction mixture as it is cooled to a temperature below about 50° C., preferably at between about 40° and 50° C. The total concentration of dissolved paraben ester in a resulting product solution is preferably in the range of from greater than 0 to about 25 weight percent based on total product solution weight, and more preferably in the range of about 2 to about 20 weight percent (same basis).

Although such a product antimicrobial solution is initially stable, on standing for a few days some crystals of presently unknown composition may develop. It has been discovered surprisingly that such a crystal development can be delayed and even completely eliminated by increasing the amount of dissolved water in an antimicrobial solution from its reaction produced level of perhaps about 1 weight percent (total solution product basis) to a value of generally not more than about 15 weight percent. Such additional water can be added at any point in the synthesis procedure. However, a present preference is to add about one-half of the added water before, during or after the paraformaldehyde dissolution step and to add the remainder to the resulting reaction mixture after the reaction is completed (which can aid in achieving cooling).

Surprisingly, the presence of the water or of the paraben ester does not adversely affect either the hydantoin formaldehyde reaction or the yield of formaldehyde substituted hydantoin. Preferably, the water and the paraben ester are both present in an antimicrobial product solution, but each can be used separately, if desired. Minor amounts of other compatible additives can be present in a solution of this invention, if desired, including, for example, inert organic solvents and other antimicrobial agents, such as sulfone-group containing compounds, isocyanurate group containing compounds and the like, such as p-tolyldiiodomethylsulfone and p-toluenesulfondichloroamide.

In general, antimicrobial solution products of this invention are cold stable to ambient temperatures of at least below about $-10°$ C., and preferably below about $-40°$ C. The inventive solutions also demonstrate useful antimicrobial activity even at concentrations of below about 1 weight percent in a medium capable of supporting microbial growth.

Presently preferred product antimicrobial solutions of this invention are characterized by having the following compositional ranges of components as shown in Table I below:

TABLE I

SOLUTION COMPOSITIONS

| Component | Weight Percent | | |
|---|---|---|---|
| | Broad Range | Preferred Range | Most Preferred Range |
| Methylol substituted 5,5-disubstituted hydantoin | 15–70[1] | 20–50 | 25–35[2] |
| Aromatic alcohol of formula (1) | 30–80 | 40–60 | 45–55[3] |
| Water | 0–15 | 2–15 | 6–10 |
| Paraben ester (total) | 0–25 | 2–20 | 3–17 |

Table I Footnotes

[1]The starting 5,5-disubstituted hydantoin is 5,5-dimethyl hydantoin and the formaldehyde condensate therewith contains a mole ratio of formaldehyde to 5,5-dimethyl hydantoin in the range of about 1:1 to about 3:1 and a content of 1,3-dimethylol-5,5-dimethyl hydantoin of at least about 10 weight percent on a total substituted hydantoin weight basis.

[2]The starting 5,5-disubstituted hydantoin is 5,5-dimethyl hydantoin and the formaldehyde condensate therewith contains a mole ratio of formaldehyde to 5,5-dimethyl hydantoin in the range of about 1.5:1 to about 2.1:1 and a content of 1,3-dimethylol-5,5-dimethyl hydantoin of at least about 25 weight percent on a total substituted hydantoin weight basis.

[3]The starting aromatic alcohol comprises phenoxyethanol.

Those skilled in the art appreciate that greater or smaller amounts of individual components can be used without departing from the spirit and scope of the present invention.

A presently most preferred practice for the present inventive process is to produce a product antimicrobial solution in which the antimicrobial liquid aromatic alcohol comprises phenoxyethanol and the 5,5-disubstituted hydantoin comprises 5,5-dimethyl hydantoin. Also, in such a product antimicrobial solution, the mole ratio between the formaldehyde and the substituted hydantoin is preferably such that the condensation product comprises on a 100 weight percent total condensation product basis at least about 10 weight percent 1,3-dimethylol-5,5-dimethyl hydantoin, and more preferably about 35 weight percent on a total condensate hydantoin weight basis.

It is preferred that an antimicrobial solution of the present invention have a measurable diluted pH in the range of about 6 to about 8.5, preferably between about 6.5 and about 7.5. The term "measured diluted pH" refers to the pH of the inventive solution when it is diluted to a solids concentration of about 10 weight percent in deionized water (or in deionized water containing about 20 weight percent isopropanol, when paraben ester is present). If it is desirable to adjust the pH of a product antimicrobial solution, the adjustment can be accomplished by addition to the solution of an aqueous acidifying agent or alkalizing agent, as the case may be during or after the synthetic reaction.

The term "alkalizing agent" refers to any commercially practical alkaline base which does not interfere with the preparation of the antimicrobially active preservative solution and which, if present in an amount in excess of that needed for pH adjustment, is preferably soluble in the solvent medium and is substantially nontoxic to humans. For example, the alkalizing agent can be an alkali metal hydroxide, such as sodium hydroxide or potassium hydroxide; an alkali metal salt, such as sodium carbonate or sodium methylate; an alkaline earth hydroxide, such as calcium hydroxide or magnesium hydroxide, or an organic base, such as a water-soluble alkylamine or an alkanolamine having 1 to about 4 carbon atoms in the alkyl or alkanol radical commonly used in cosmetics, such as dimethylamine, diethylamine, monoethanolamine, diethanolamine, triethanolamine, monoisopropanolamine, diisopropanolamine, triisopropanolamine and the like. Sodium hydroxide is particularly preferred and is added as a concentrated, caustic solution of about 50 weight percent. Thus, less than about 1 weight percent caustic solution is generally needed.

Likewise, the term "acidifying agent" refers to any commercially practical acid that does not interfere with the preparation of the antimicrobially active preservative solution and, which if present in an amount in excess of that needed for pH adjustment, is preferably soluble in the solvent medium and is substantially nontoxic to humans. For example, acids commonly used in cosmetics include organic water-soluble polyhydroxy acids, such as lactic acid, citric acid, and tartaric acid; and inorganic acids, such hydrochloric acid, phosphoric acid and sulfuric acid.

As indicated above, and as demonstrated and illustrated by the following examples, the preferred compositions of Table I are characterized by synergistic coaction between the solvent compound(s) of formula (1) and the solute formaldehyde substituted hydantoin compound(s).

The term "antimicrobial preservative" or "antimicrobial solution" as used refers to a composition that can kill, prevent, inhibit or retard the growth and reproduction of microorganisms when it is included in a product medium at a concentration sufficient to prevent spoilage or prevent the growth of an inadvertently added microorganism (that is, an antimicrobially effective amount). Such an antimicrobial preservative generally extends the useful life of a product without contributing otherwise to the claimed efficacy of the product.

The preservation efficacy of the inventive antimicrobial solution was determined by in vitro microbial challenge testing when it was employed in an aqueous product formulation known to support microbial growth. Briefly, the challenge test protocol consists of inoculating the product formulation with different types of microorganisms which are representative of the most frequently encountered contaminants in cosmetic and personal care formulations. After the formulation was inoculated, microbial content was periodically determined over a period of at least 14 days or more.

The goal was to achieve a reduction in the average count of microbial colony forming units (cfu) per milliliter (ml) of test product to less than 10 of each test microorganism. When the average count for cfu/ml reaches less than 10, a product is generally considered to be adequately preserved. Thus, the effective amount of antimicrobial preservative solution for adequately preserving the test product in the 14 day time period was deemed to be the minimum effective level (MEL). It is recognized in the trade that a formulation can be unnecessarily over preserved when the amount of preservative employed exceeds the amount required for adequate preservation.

As illustrated in the examples below, it was surprisingly found that in a shampoo product model, the MEL for an inventive antimicrobial solution prepared by the present method was achieved at a concentration which was about 40 percent lower than the MEL amount of an antimicrobial solution of comparative formaldehyde substituted hydantoin concentration prepared by the method disclosed in U.S. Pat. No. 5,037,843 employing a polyhydroxy alcohol solvent medium.

In the cosmetic, personal care and pharmaceutical arts, the representative microorganisms of greatest concern include, but are not limited to, molds, such as *Aspergillus niger* (An); yeasts, such as *Candida albicans* (Ca); gram-positive microorganisms, such as *Staphylococcus aureus* (Sa); nonfermentative gram-negative rod microorganisms, such as *Pseudomonas aeruginosa* (Pa) and fermentative gram-negative rod microorganisms, *Escherichia coli* (Ec).

A discussion of the various microorganisms of particular concern in consumer products generally can be found in Muscatiello M. J., "CTFA's Preservation Guidelines," *Cosmetics & Toiletries*, 108, 53, 56–59 (1993), the relevant portions of which are incorporated herein by reference. Likewise, those skilled in the art are familiar with the various challenge tests employed for determining antimicrobial activity and minimum effective levels. See, for example, the discussions of various testing by Mulberry G. K, et al. in "Rapid Screening Methods for Preservative Efficacy Evaluations," *Cosmetics & Toiletries*, 102, 47–50, 51–54 (1987) and by Parsons, T, in "A Microbiology Primer for the Microbiology Manager," *Cosmetics & Toiletries*, 105, 73–77 (1990), the relevant portions of each of which are incorporated herein by reference.

The following Examples illustrate methods and liquid antimicrobial solutions of this invention with generally preferred ingredients and procedural steps, but are not intended to limit the invention.

EXAMPLE 1

This example illustrates one method embodiment of preparing a substantially anhydrous liquid antimicrobial solution containing about 68 weight percent 1,3-dimethylol-5,5-dimethyl hydantoin (DMDM Hydantoin) prepared in phenoxyethanol from the following component mixture:

| Component | Weight Percent (as supplied) |
|---|---|
| 1. Phenoxyethanol | 31.1 |
| 2. Paraformaldehyde Prills (95%) | 22.7 |
| 3. 5,5-Dimethyl hydantoin (96%) | 45.6 |
| 4. Sodium hydroxide (50% in water) | 0.6 |

Ingredient no. 1 was charged into a sealable reaction vessel outfitted with a jacket for heating or cooling and a mixing agitator. Next, ingredients no. 2 and 3 were sequentially added and dissolved with mixing agitation subsequently followed by admixing in ingredient no. 4. Then, while continuing the mixing agitation, the composition was heated to about 105° C. The reactor was then sealed to prevent loss of volatile components, and formaldehyde in particular, from the heated reaction mixture.

The heated reaction mixture was maintained at the foregoing temperature under mixing agitation over a reaction period of about 12 to about 18 hours, until the desired concentration of DMDM Hydantoin was produced. A portion of the heated clear reaction mixture was periodically sampled and cooled for determining the measurable diluted pH and free formaldehyde.

The measurable diluted pH was determined with about 10 grams of sample diluted with about 90 grams of deionized water and was between about pH 6.5 and about 7.5. The reaction was judged completed when the amount of free formaldehyde was below about 2 weight percent of the total reaction mixture. The reaction mixture was then cooled to about 25° C., assayed and collected.

The liquid DMDM Hydantoin containing antimicrobial solution obtained by this method was a substantially water-white visually clear liquid. On standing at ambient room temperature for about 5 days, some crystals of unknown composition were observed.

EXAMPLE 2

This example illustrates the preparation of a substantially stable liquid antimicrobial solution of this invention containing about 57.8 weight percent 1,3-dimethylol-5,5-dimethyl hydantoin (DMDM Hydantoin), about 26.4 weight percent phenoxyethanol and about 15 weight percent methyl paraben from the following component mixture:

| Component | Weight Percent |
|---|---|
| 1. DMDM Hydantoin containing solution of Example 1 | 85 |
| 2. Methylparaben | 15 |

The methyl paraben was added directly into component no. 1 with stirring and warming to about 50° C. to hasten solubilization. The resulting liquid antimicrobial solution was substantially clear with no crystals observed on standing for about 14 days at ambient room temperature.

EXAMPLE 3

This example illustrates another method embodiment of preparing a liquid antimicrobial solution containing about 30 weight percent DMDM Hydantoin prepared in phenoxyethanol from the following component mixture:

| Component | Weight Percent (as supplied) |
| --- | --- |
| 1. Phenoxyethanol | 48 |
| 2. Paraformaldehyde Prills (95%) | 9.72 |
| 3. 5,5-dimethyl hydantoin (96%) | 21.78 |
| 4. Methyl Paraben | 11 |
| 5. Propyl Paraben | 3 |
| 6. Water, deionized | 6.5 |

Component no. 1 and half the amount of component no. 6 were each charged into a sealable reaction vessel outfitted with a jacket for heating or cooling and a sampling port and were admixed with stirring. Component no. 2 was then added slowly with stirring to the liquid mixture in the reactor. The resulting liquid medium was then heated to about 40° C. Component no. 3 was then added slowly to the so-heated liquid medium to form a reaction mixture. The reactor was then sealed to prevent loss of volatile components, and formaldehyde in particular, from the reaction mixture during heating. The resulting reaction mixture was then heated to about 105° C. and maintained at that temperature.

After about one hour of heating, the reaction mixture was sampled, the measurable diluted pH determined and free formaldehyde was determined. The diluted pH was measured as described in Example 1. Heating was subsequently maintained and the reaction mixture was periodically sampled as before over a reaction period of about 2 to about 4 hours. The reaction was judged completed when the desired amount of DMDM Hydantoin was produced and the free formaldehyde concentration was below about 2 weight percent of the total weight of the reaction mixture.

The reaction mixture was then cooled to between about 45° and about 50° C. Component nos. 4 and 5 were then admixed into the so-cooled reaction mixture with stirring until the resulting reaction mixture was homogeneous.

The reaction mixture was then sampled and the remaining amount of component no. 6 was added. Mixing agitation was subsequently continuously maintained until a homogeneous, substantially clear liquid solution was produced.

Thereafter, the liquid solution was then cooled to about 25° C., filtered through a 0.5 micron filter and collected.

A substantially cold-stable, water-white clear liquid antimicrobial solution was obtained having a cloud point of between about −10° and about −40° C. The product liquid antimicrobial solution had a measurable diluted pH of between about 6.5 and about 7.5 when 10 grams of liquid sample were diluted with 90 grams of a 20 weight percent isopropanol in water solution. The assayed amount of free formaldehyde was between about 0.9 and about 2 weight percent and the assayed amount of water was between about 7 and about 8 weight percent on a total solution basis.

EXAMPLE 4

To demonstrate the preservative efficacy of the liquid antimicrobial solution of Example 3 containing about 30% DMDM Hydantoin in about 48% phenoxyethanol, various concentrations ranging from 0 (control) to about 1 weight percent were employed in a "mild" shampoo model having the following composition:

| Component | Weight Percent (as supplied) |
| --- | --- |
| Ammonium lauryl sulfate (30%) | 8 |
| Disodium oleamido MEA sulfosuccinate (35%) | 2 |
| Hydrolyzed animal protein (55%) | 4 |
| Polysorbate 80 | 2 |
| Cocamide DEA | 1 |
| Water, deionized | 83 |
| Citric acid to pH 7–7.5 | q.s. |
| Liquid antimicrobial solution of Ex. 3 | 0 to 1 |

Microbial efficacy was assessed by carrying out modified challenge tests for the inhibition of the growth of the mold, *Aspergillus niger* (An) ATCC No. #16404; the yeast, *Candida albicans* (Ca) ATCC No. #10231; and a mixed bacterial culture of *Staphlococcus auerus* (Sa) ATCC No. #6538, *Pseudomonas aeruginosa* (Pa) ATCC No. #9027 and *Escherichia coli* (Ec) ATCC No. #8739. A series of test shampoos were prepared containing 0%, 0.2%, 0.4%, 0.6%, 0.8% and 1% of the liquid antimicrobial solution of Example 3.

A series of samples of about 20 ml of each test shampoo were each separately inoculated with about $10^5$ to $10^6$ cfu/ml of An, of Ca and of mixed bacterial culture of Sa, Pa, Ec organisms. The test shampoo samples were individually plated out in tryptic soy agar medium with lecithin and Polysorbate 80 for assessing bacterial growth and in potato dextrose agar (acidified) for assessing fungi growth. Following platings at day 1 and day 14 and incubation, readings of the number of colony forming units per milliliter (cfu/ml) were made. When the test organism count was less than 10 cfu/ml, the test shampoo product was judged to be adequately preserved.

The microbial efficacy data after 14 days was as follows:

| % Liq. of Ex. 3 in Test Shampoo | Colony Forming Units (cfu/ml) | | |
| --- | --- | --- | --- |
| | An | Ca | Sa, Pa, Ec |
| 0.2 | $10^4$ | $10^5$ | <10 |
| 0.4 | <10 | $10^5$ | <10 |
| 0.6 | <10 | <10 | <10 |
| 0.8 | <10 | <10 | <10 |
| 1 | <10 | <10 | <10 |
| 0 (control) | $10^5$ | $10^5$ | $10^6$ |

The 14 day data show that the inventive liquid antimicrobial solutions of this invention demonstrated antimicrobial effectiveness, which increased as the added concentration of such liquid solution was increased to about 0.6%. Based on this data, the test shampoo product was judged adequately preserved at a 0.6% concentration, so this concentration was considered to be the minimum effective level (MEL).

For comparison, a second similar series of test shampoos were prepared each separately containing about 0.6%, 0.8% and 1% of liquid antimicrobial solution containing about 30 weight percent of DMDM Hydantoin; 56 weight percent propylene glycol; 11 weight percent methyl paraben and 3 weight percent propyl paraben. This solution was prepared by the method disclosed by Schoenberg in U.S. Pat. No. 5,037,843. These test shampoos were included and were similarly subjected to preservative challenge testing in the foregoing study.

The microbial efficacy data after 14 days was as follows:

| % Liq. of '843 in Test Shampoo | Colony Forming Units (cfu/ml) | | |
|---|---|---|---|
| | An | Ca | Sa, Pa, Ec |
| 0.6 | <10 | $10^5$ | <10 |
| 0.8 | <10 | $10^3$ | <10 |
| 1 | <10 | <10 | <10 |
| 0 (control) | $10^5$ | $10^5$ | $10^6$ |

The 14 day data show that a minimum effective level of about 1% of the '843 solution was needed to achieve adequate preservation.

At a concentration of about 0.6%, the liquid antimicrobial solution of Example 3 provided a use concentration of about 0.18% DMDM Hydantoin, about 0.29% phenoxyethanol, and about 0.08% total paraben in the shampoo model. This use concentration for the phenoxyethanol is less than the generally recommended minimum level of about 0.5% when phenoxyethanol is used alone.

A comparison of these 14 day data for the '843 solution and the Example 3 solution shows surprisingly that the inventive liquid antimicrobial solution of Example 3 was about 1.5 to about 1.7 times more effective than the liquid antimicrobial solution prepared with propylene glycol by the method of the '843 patent.

Based on these data, lesser amounts of liquid antimicrobial solutions of this invention were more effective in achieving substantially complete microbial reduction to <10 cfu/ml than were greater amounts of liquid antimicrobial solution containing DMDM Hydantoin prepared in a propylene glycol medium. For example, the efficacy achieved at a concentration of about 0.4% and about 0.6% with the inventive solution of Example 3 was equal to a concentration of about 0.6% and about 1% of the antimicrobial solution of the '843 patent respectively. Hence, an amount of about 40% less of the inventive liquid antimicrobial solution was needed to achieve adequate preservation when the inventive solution was employed.

Thus, the enhanced antimicrobial efficacy of the inventive solutions observed in this comparative study was surprising.

The present invention has been described generally and with respect to preferred embodiments. It will be understood that modifications and variation of the disclosed method and compositions may be made without departing from the spirit and scope of the novel concept of the present invention.

What is claimed is:

1. A method for preparing an antimicrobial solution of a formaldehyde substituted hydantoin comprising the steps of sequentially:

(a) dissolving a formaldehyde selected from the group consisting or paraformaldehyde and formalin in at least one liquid aromatic alcohol having the formula:

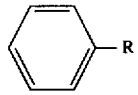

where R is selected from the group consisting of —CH$_2$OH, —OCH$_2$—OH, —OCH$_2$CH$_2$OH, —CH$_2$CH$_2$OH, —OC$_3$H$_6$OH, and —C$_3$H$_6$OH to provide a liquid medium containing at least about 2 weight percent 100 weight percent total formaldehyde on a calculated liquid medium basis;

(b) heating said liquid medium to a temperature in the range of about 35° to about 55° C. to provide a heated liquid medium;

(c) admixing into said heated liquid medium, a 5,5-disubstituted hydantoin wherein each such substituent is independently selected from the class consisting of phenyl and lower alkyl groups containing less than 7 carbon atoms per group to provide a reaction mixture, the amount of said hydantoin so admixed being sufficient to produce in said reaction mixture an initial calculated mole ratio of formaldehyde to said hydantoin of about 1:1 to about 3:1;

(d) further heating under autogenous conditions said reaction mixture to a temperature in the range of about 80° to about 110° C. and maintaining said temperature until the reaction between said paraformaldehdye and said hydantoin is substantially complete, thereby to attach methylol functional groups to at least one of the two nitrogen atoms of the ring of said hydantoin, the amount of free formaldehyde present in said resulting reaction mixture being below about 2 weight percent based on the total weight of said resulting reaction mixture; and (e) thereafter cooling said resulting reaction mixture to provide said antimicrobial solution, said antimicrobial solution being characterized by:

(1) containing a condensation product of said paraformaldehyde and said hydantoin wherein methylol functional groups are attached to at least one of the two nitrogen atoms of the ring of said hydantoin; and (2) having the capacity to inhibit and/or retard the growth of microorganisms when an effective antimicrobial amount of said antimicrobial solution is subsequently included in a medium capable of supporting growth of said microorganisms.

2. The process of claim 1 wherein said antimicrobial solution additionally contains about 1 to about 15 weight percent water based on total weight of said antimicrobial solution, said water having been added in at least one of said steps (a) through (e).

3. The process of claim 1 wherein said antimicrobial solution additionally contains from greater than 0 to about 25 weight percent of at least one dissolved paraben ester, said paraben ester having been added in at least one of said steps (a) through (e).

4. The process of claim 1 wherein said antimicrobial solution additionally contains from greater than 0 to about 25 weight percent of at least one dissolved paraben ester, said paraben ester having been added in at least one of said steps (a) through (e).

5. The process of claim 4 wherein said paraben ester is added in said step (3) by first cooling said reaction mixture to a temperature in the range of about 40° to about 50° C., then dissolving said paraben ester in said so partially cooled reaction mixture, and thereafter cooling said resulting reaction mixture to ambient temperature.

6. The process of claim 1 wherein said antimicrobial solution is filtered.

7. The process of claim 1 wherein said antimicrobial solution is adjusted by addition thereto of an aqueous acidifying or alkalizing agent in an amount sufficient to produce a dilution pH in the range of about 6 to about 8.5.

8. The process of claim 2 wherein:

(a) said liquid aromatic alcohol is phenoxyethanol;

(b) said 5,5-disubstituted hydantoin is 5,5-dimethyl hydantoin; and (c) said calculated mole ratio of said formaldehyde to said hydantoin is such that said condensation product comprises at least about 10 weight percent 1,3-dimethylol-5,5-dimethyl hydantoin.

9. The process of claim 8 wherein said antimicrobial solution additionally contains about 3 to about 15 weight percent of dissolved paraben esters.

10. The antimicrobial solution produced by the process of claim 1, and wherein on a 100 weight percent solution basis:
   (a) the amount of said aromatic alcohol is in the range of about 30 to about 80 weight percent; and
   (b) the amount of said methylol substituted 5,5-disubstituted hydantoin is in the range of about 30 to about 80 weight percent.

11. The antimicrobial solution produced by the process of claim 4, and wherein on a 100 weight percent solution basis:
   (a) the amount of said aromatic alcohol is in the range of about 40 to about 60 weight percent;
   (b) the amount of said methylol substituted 5,5-disubstituted hydantoin is in the range of about 20 to about 50 weight percent;
   (c) the amount of said water is in range of about 2 to about 15 weight percent; and
   (d) the amount of said paraben ester is in the range of about 2 to about 20 weight percent.

12. The antimicrobial solution produced by the process of claim 9 and wherein on a 100 weight percent solution basis:
   (a) the amount of said phenoxyethanol is in the range of about 45 to about 55 weight percent;
   (b) the total amount of said dimethylol substituted 5,5-dimethyl hydantoin is in the range of about 25 to about 35 weight percent, and the formaldehyde condensate therewith contains a mole ratio of formaldehyde to 5,5-dimethyl hydantoin in the range of about 1.5:1 to about 2.1:1 and a content of 1,3-dimethylol-5,5-dimethyl hydantoin of at least about 10 weight percent; and
   (c) the amount of said water is in the range of about 6 to about 10 weight percent.

13. A method of inhibiting or retarding microbial growth in a medium capable of supporting microorganism growth, said method comprising incorporating into said medium an antimicrobially effective amount of said antimicrobial solution of claim 10.

* * * * *

UNITED STATES PATENT AND TRADEMARK OFFICE
CERTIFICATE OF CORRECTION

PATENT NO. : 5,616,722

DATED : April 1, 1997

INVENTOR(S) : Schoenberg, et al.

It is certified that error appears in the above-indentified patent and that said Letters Patent is hereby corrected as shown below:

Col. 11, line 52 (claim 1), change "or" to --of--.
Col. 11, line 63 (claim 1), cancel "100 weight percent".
Col. 11, line 64 (claim 1), after "calculated" insert --100 weight percent--.
Col. 12, line 13 (claim 1), change "paraformaldehyde" to --formaldehyde--.
Col. 12, line 17 (claim 1), before "resulting" delete "said" and insert --the--. Same line, after "resulting" insert --said--.
Col. 12, lines 24-25 (claim 1), change "paraformaldehyde" to --formaldehyde--.
Col. 12, line 49 (claim 5), change "(3)" to --(d)--.
Col. 13, line 18 (claim 11), after "in" insert --the--.

UNITED STATES PATENT AND TRADEMARK OFFICE
CERTIFICATE OF CORRECTION

PATENT NO. : 5,616,722
DATED : April 1, 1997
INVENTOR(S) : Schoenberg, et al.

It is certified that error appears in the above-indentified patent and that said Letters Patent is hereby corrected as shown below:

Col. 14, after line 20 (and after claim 13), add claim 14:

--14. The process of claim 1 wherein said liquid aromatic alcohol is selected from the group consisting of phenoxyethanol, benzylalcohol, phenethyl alcohol and phenoxyisopropyl alcohol.--

Signed and Sealed this

Fifteenth Day of July, 1997

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO.   : 5,616,722
DATED        : April 1, 1997
INVENTOR(S)  : Schoenberg, et al.

It is certified that error appears in the above-identified patent and that said Letters Patent is hereby corrected as shown below:

Col. 12, after line 43 (claim 4), change "1" to --2--.

Signed and Sealed this

Twenty-fourth Day of November, 1998

Attest:

BRUCE LEHMAN

Attesting Officer

Commissioner of Patents and Trademarks